United States Patent [19]

Frank

[11] 3,996,927

[45] Dec. 14, 1976

[54] BLOOD PRESSURE MONITOR LEVELING DEVICE

[75] Inventor: Ulrich Anton Frank, Princeton, N.J.

[73] Assignee: Hoffmann-La Roche Inc., Nutley, N.J.

[22] Filed: June 27, 1975

[21] Appl. No.: 591,256

[52] U.S. Cl. .................. 128/2.05 D; 33/292; 128/2.05 E
[51] Int. Cl.² .......................................... A61B 5/02
[58] Field of Search ............ 128/2.05 D, 2.05 E; 33/292

[56] References Cited

UNITED STATES PATENTS

| 297,164 | 4/1884 | Randolph | 33/292 |
|---|---|---|---|
| 1,187,249 | 6/1916 | Brown | 33/292 |
| 2,600,324 | 6/1952 | Rappaport | 128/2.05 D X |
| 2,941,297 | 6/1960 | Howley et al. | 33/292 |
| 3,517,445 | 6/1970 | Harris | 33/292 X |
| 3,590,809 | 7/1971 | London | 128/2.05 D |
| 3,590,818 | 7/1971 | Lemole | 128/2.05 D |
| 3,602,214 | 8/1971 | London et al. | 128/2.05 D |
| 3,636,942 | 1/1972 | Nye | 128/2.05 D |
| 3,690,312 | 9/1972 | Leibinsohn | 128/2.05 D |

Primary Examiner—Kyle L. Howell
Attorney, Agent, or Firm—Samuel L. Welt; Bernard S. Leon; Mark L. Hopkins

[57] ABSTRACT

An elevation and leveling adjustment arrangement for accurately locating pressure-to-current transducers, used in monitoring blood pressure during and post surgery, at an appropriate reference point relative to the patient. The pressure-to-current transducers are mounted to a platform or base which also has provided thereon level indicating means and optical means. The optical means in combination with the level indicating means is arranged to indicate when the base is properly leveled and the pressure transducers are at the same elevation as the reference point marked on the patient. In the case where an optical sighting means is employed, the reference point is directly viewable thereby. The platform further includes leveling adjust means which adjustably couples the base to a telescoping elevation adjust means, the latter of which provides fine elevation adjustment of the platform.

6 Claims, 4 Drawing Figures

BLOOD PRESSURE MONITOR LEVELING DEVICE

BACKGROUND OF THE INVENTION

The present invention relates to leveling mechanisms and more particularly to an adjustable leveling arrangement for enabling the placement of critical components required in support functions for patient surgery, for example heart surgery, and also in post operative care, at a precise position relative to a predetermined reference point, such as the right atrium of the patient.

In most instances of patient surgery and recovery apparatus is employed to accurately monitor the patient's blood pressure. Frequently atrial and/or arterial blood pressure monitoring is necessary, for example, through catherization techniques. Pressure-to-current transducers are usually employed in such monitoring.

In preparation of the pressure-to-current transducers for taking atrial and/or arterial blood pressures of a prone patient, the transducers must be positioned at the same level as some reference point, generally the right atrium. This point is marked on the chest of the patient. Heretofore, following the marking of the patient's chest, a carpenter's level bar or the like has been used to bring the transducers to that level, as mounted on a vertical stand.

Adjustment of the elevation of the transducers via this means is prone to error. Moreover, such a technique requires the use of bulky equipment, as the patient may be several feet away from the equipment stand on which the transducers are mounted. In addition, such means provide inherent equipment storage problems, such that the same is often not conveniently available when needed.

SUMMARY OF THE INVENTION

It is, therefore, a principle object of this invention to provide a means of accurately performing the above-mentioned surgery assistance or post operative function while overcoming the above-indicated drawbacks to the prior art.

Another object of this invention is to provide a simple and inexpensive arrangement wherein the transducer mounting means and elevation and level adjusting means are provided in a single integrated arrangement.

A further object of this invention is to provide an arrangement capable of handling several transducers for the same patient simultaneously, with high accuracy and complete patient safety.

According to the broader aspects of the invention there is provided an arrangement for providing at least one pressure indicating means, such as a transducer, used in atrial and/or arterial blood pressure determination, at the same level as a pre-established remote reference point on a patient whose blood pressure is to be determined, comprising a base adjustable to provide a surface level with the horizontal and having removably mounted thereto said at least one pressure indicating means first means operatively connected to said base for controllably varying the elevation of the base relative to said remote reference point without disturbing the leveling of said base; and second means adjustably mounted on said platform for determining when a predetermined portion of said at least one pressure indicating means is elevated level with said remote reference point on the patient.

The invention provides a base or platform mounted on a vertically adjustable telescoping support arrangement, with the base having clamping means for rigidly securing a number of pressure-to-current transducers, as well as a leveling indicator and optical means combination for enabling an operator to adjust the mechanism relative to the reference point on the patient. The telescoping support is itself adjustably clamped to a vertical pole stand, thus permitting gross as well as fine elevation adjustments. The leveling indicator means is used initially to ensure that the platform or base is adjusted level relative to the horizontal regardless of the possible unevenness of the floor.

BRIEF DESCRIPTION OF THE DRAWING

The above-mentioned and other objects of this invention will become more apparent by reference to the following description taken in conjunction with the accompanying drawings, in which.

DESCRIPTION OF THE PREFERRED EMBODIMENT(S)

Figure 1:
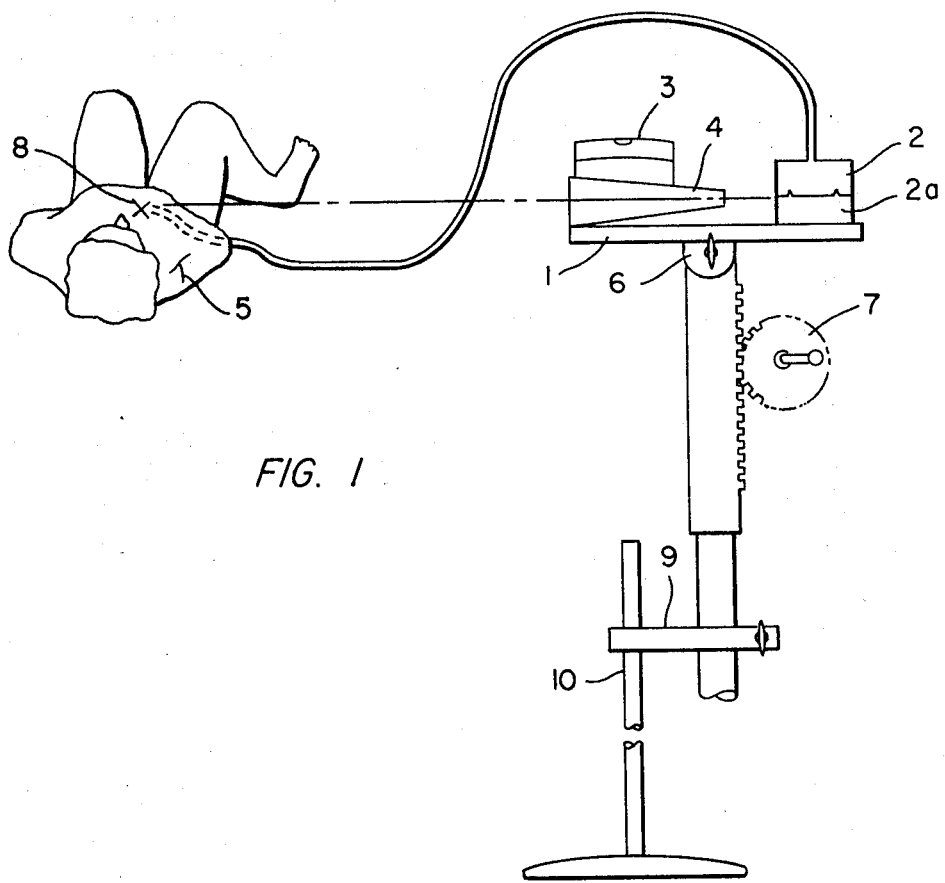
FIG. 1 schematically illustrates the apparatus according to the invention in connection with a prone patient.

FIG. 1 illustrates apparatus according to the invention connected and referenced to a prone patient. A platform or base 1 has demountably but rigidly mounted thereon the pressure-to-current transducer(s) 2 used to monitor atrial and/or arterial blood pressure, which transducer(s) have to be leveled to the patient's right atrium. This is indicated in FIG. 1 by the X on the patient's chest at 8. Also rigidly, but nevertheless adjustably, mounted on the platform 1 are a leveling indicator 3 and an optical means 4 such as an optical sighting means, wherein the former is fixedly secured to the latter. Optical means 4 is employed to establish the level line from the platform or base 1 to the patient 5.

The arrangement also includes level adjust means 6, for example a wing nut arrangement or other appropriate means, employed to enable adjustment of the platform relative to the horizontal yet be tightened to securely maintain the selected platform orientation. Moreover, the arrangement provides elevation adjust means 7 which enable one to adjustably change the elevation of the platform without disturbing the leveling thereof as set via the leveling indicator 3 and the leveling adjust means 6. The elevation adjust 7 may be any appropriate telescoping worm-gear type adjustable support arrangement, wherein a fine elevation adjustment may be effected for example by rotating a crank handle on element 7. As shown, element 7 itself is adjustably clamped by a suitable clamping mechanism 9 to a vertical support such as an intravenous infusion pole stand 10. Clamp arrangement 9 enables one to effect gross elevational adjustments for the platform or base 1 by permitting movement between the pole stand 10 and the telescoping element 7.

Figure 2A:
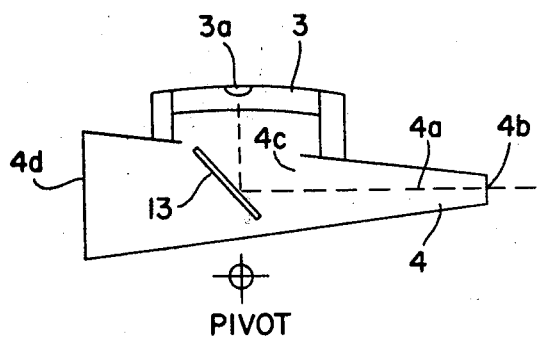
FIG. 2A is a schematic enlargement of the level indicating and optical sighting means of the invention.
Figure 2B:
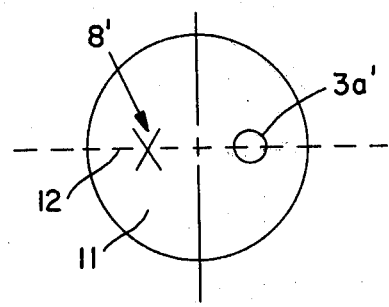
FIG. 2B is a diagram showing the view of the observer looking into the optical sighting means when a correct positioning of the transducer is obtained.

The operation of the example arrangement of the invention depicted in FIG. 1 will be explained in connection with the illustrations in FIGS. 2A and 2B, wherein there is shown respectively: a somewhat enlarged schematic representation of the optical sight means 4 together with the level indicating means 3, which as shown in FIG. 2A may be of the bubble indicator type; and an illustration of the view of the observer as seen through the optical sighting means of FIG. 2A when the transducers are at the proper position relative to the reference point 8 on the patient 5. FIG. 2A represents one preferred arrangement of optical sighting means wherein a split view is provided to yield a field of view 11 of both the bubble 3a of level indicating means 3 and the X on the patient's chest.

As a starting point, the pole stand 10 is placed somewhere in the vicinity of the patient 5. It is entirely possible that the floor is not level. The elevation adjust means 7 is assembled to the pole stand 10 via clamp 9.

The pressure-to-current transducer(s) 2 are secured to the base or platform 1 by any suitable appropriate means such that the critical element of each, i.e. the pressure diaphram (schematically indicated at 2a), which would in the instance of this invention be arranged with its broad surfaces parallel to the horizontal, is placed as nearly exactly level as possible to the sight path 4a of the sighting means 4. This is effected for example by placing the transducers in respective securing means such that the level of the pressure diaphrams thereof rest at a selected height above the base of platform 1. The sight 4 which is adjustably secured to the platform 1 is then raised or lowered to this height.

One or more line indicators may be inscribed or drawn on the sight adjustment bracket or at other appropriate places to enable the operator to ascertain that the platform and the leveling indicator are oriented parallel with one another.

The base 1 is then mounted unto the telescoping portion of the elevation adjust means 7, via the leveling adjust means 6. At the same time the operator may observe the leveling indicator 3 and make an appropriate adjustment of adjust means 6 to enable the base 1 to be exactly parallel to the horizontal regardless of the tilt of the floor and/or the pole stand 10.

At this point in the assemblage of the invention, the optical means 4, the platform 1 and the pressure-to-current transducer diaphrams 2a have been rendered level, i.e. parallel to the horizontal.

The gross elevation adjustment may then be made (with the worm gear of adjust means 7 initially at midpoint) by loosening the clamp arrangement 9 holding the telescoping adjust 7 to the pole stand 10 and moving the platform/elevation adjust means combination up or down until an elevation is reached somewhere near the elevation of the reference point X marked on the chest of the patient 5 at 8.

Figure 3:
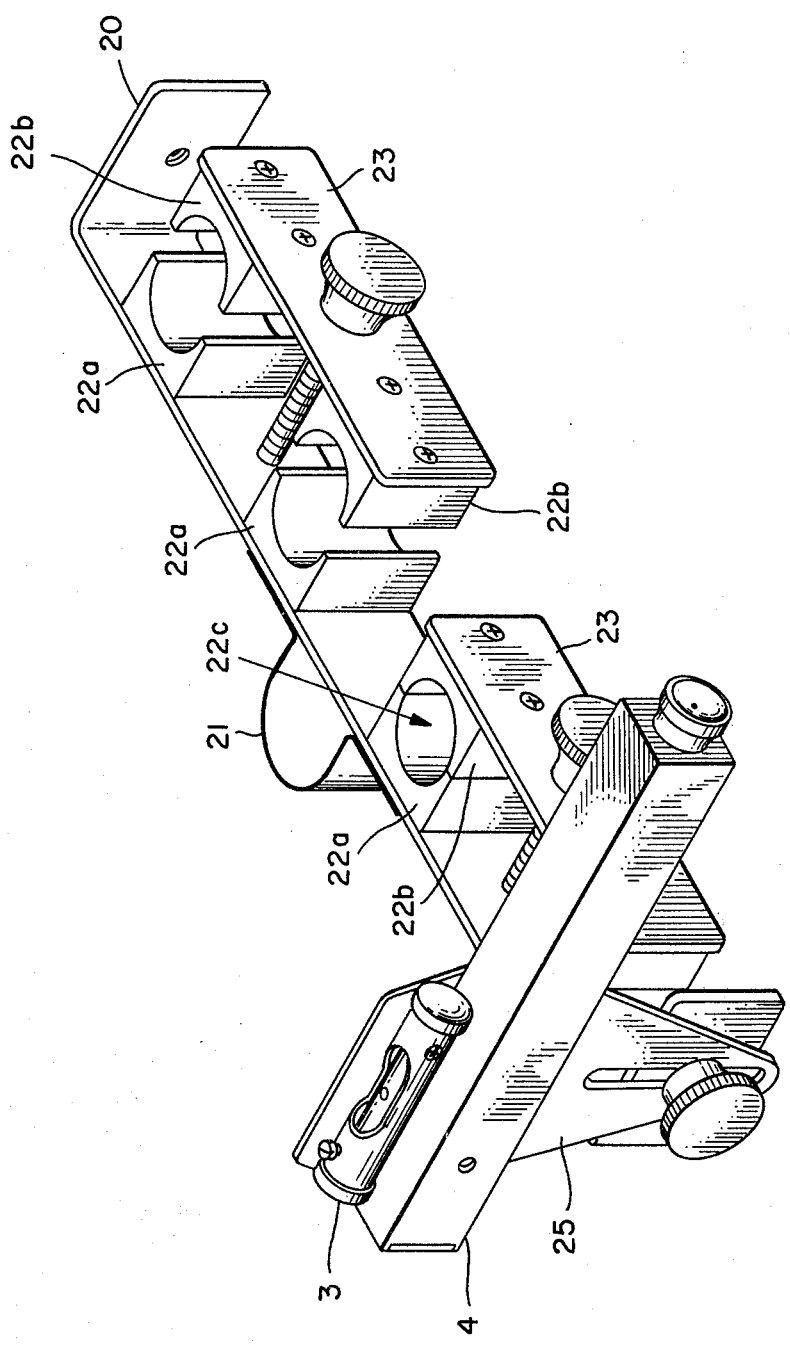
FIG. 3 is a perspective illustration of an embodiment of the invention showing the platform assembly removed from the telescoping support.

Where, as in the case of the example embodiment depicted in FIGS. 1–3, an optical sighting means is employed, a fine adjustment may now be made by looking into the sight 4, which provides a retical line 12. The image 3a' of the bubble 3a of level indicator means 3 is reflected by a mirror 13 along the line of sight of optical sight means 4 to appear centered on the retical and off to one side of the field of view 11. Sight 4 in this example embodiment is a dual sighting mechanism wherein mirror 13 is dimensioned to occupy only one-half of the line of sight through element 4. The observer at 4b sees the bubble through the open slot 4c in sight 4. The other half of the observer's view constitutes what is observed through the other end 4d of sight 4, which in accordance with the invention is intended to be the reference mark X on the chest of the patient.

Looking into sight 4, the operator varies the fine elevation adjust means 7 up or down until the X on the patient's chest is viewed through the sight as lying squarely on the retical line 12 at 8' opposite the bubble reflection 3a'. At this point the transducer(s) 2 are positioned at the exact elevation of the reference point on the patient. The leveling of the platform relative to the horizontal (and thereby the sight 4) as well as the leveling of the diaphrams 2a of transducer(s) 2 relative to the platform, assure that elevation misadjustments are eliminated.

FIG. 3 illustrates in perspective an embodiment of the invention, wherein the platform constitutes a U-shaped main bracket 20 having mounted on the rear side thereof an adjustable clamping means 21 for receiving the upper end of a portion of the telescopic elevation adjust means 7. To the front or inner side of the base constituting the U-shaped elongated bracket 20 are a plurality (in this case four) of dielectric members 22a having a flat rear surface for flush mounting to bracket 20 (e.g. by screws) and a cylindrically concave surface on the front side thereof. Members 22a cooperate with respective ones of a like number of similarly shaped but oppositely arranged members 22b to form a largely cylindrical channel 22c therebetween. Each pair 22 of members 22a and 22b constitutes a receiving means for the pressure-to-current transducers(s) 2. The members 22b are mounted to respective holders 23 (in this case one holder is illustrated for each pair of members 22) each of the latter of which, via a screw adjust engaging bracket 20, form a vise-like arrangement for securing the transducers to the platform or base 20. Members 22a and 22b are made of any suitable dielectric material to ensure proper electrical isolation of the transducers from earth ground Either side of the U-shaped bracket 20 is provided as a mount for the optical means 4 and level indicator 3. In the arrangement of FIG. 3, a somewhat diamond-shaped member 25 is illustrated, having fixedly mounted thereto (e.g. by screws) in parallel the level indicator 3 and a sight 4. Member 25 is adjustably secured to bracket 20 by a screw adjust which cooperates with an elongated slot in member 25. Thereby, the indicator 3 and sight 4 may be rotated or elevated relative to the base 20 via a corresponding adjustment of member 25 about its screw adjust.

Horizontal lines may be inscribed or drawn on member 25 indicating the proper height thereof above the top edge of bracket 20 for a particular kind of pressure-to-current transducer, wherein adjustment of member 25 via said line will ensure that the level indicator and the sight are in parallel with the top edge of the bracket 20 and at a proper height relative to the pressure diaphram for a given make of transducer. Bracket 20 member 25, clamping means 21 and holders 23 may all be made of a suitable light weight metal. The sight 4 and bubble indicator 3 may be, for example, the commercially available Model Abney Level made by Edmund Scientific Co. of Barrington, N.J.

Alternatively, the optical means 4 may be a collimated (i.e. narrow) light beam source. In this example a source of light in combination, for example, with a suitable lens provides a narrow light beam used to illuminate the reference point X in the patient. Thus, in this embodiment the light beam substitutes for the sight path of optical sight means 4. The light beam source is fixedly combined with the level indicating means such that the latter is parallel with the light beam. When the beam of light illuminates the reference mark on the patient the proper elevation for the pressure transducers is achieved. One example of optical means generating a narrow light beam useful in this invention would be a conventional low power laser.

The principles of this invention are, moreover, applicable to the accurate positioning of the zero reference marker of one or more manometers relative to, for example, the right atrium of the patient, wherein the manometer(s) may be ultimately adjustably coupled to a vertical stand.

I claim:

1. An arrangement for providing at least one pressure indicating means, such as a transducer, used in atrial and/or arterial blood pressure determination, at the same level as a pre-established remote reference point on a patient whose blood pressure is to be determined, comprising:

a base adjustable to provide a surface which is level with the horizontal and having removably mounted thereto said at least one pressure indicating means;

first means operatively connected to said base for controllably varying the elevation of the base relative to said remote reference point without disturbing the leveling the said base; and second means adjustably mounted on said base relative to said surface thereof for determining that a predetermined portion of said at least one pressure indicating means is elevated level with said remote reference point on the patient, said second means including third means adjustably mounted relative to said surface of said base for indicating said predetermined portion of said at least one pressure indicating means is elevated level with said remote reference point and level indicating means fixedly mounted relative to said third means for indicating when said second means is operatively level with the horizontal.

2. The arrangement according to claim 1 wherein said first means includes a worm gear adjustment means in operative connection with a telescoping shaft.

3. The arrangement according to claim 2 further including means for pivoting said base relative to said shaft.

4. The arrangement according to claim 1 wherein said third means constitutes optical sighting means.

5. The arrangement according to claim 4 wherein said optical sighting means includes guidance means for indicating the relative change in elevation required between said at least one pressure indicating means and said remote reference point to bring said predetermined portion of said pressure indicating means level with said pre-established remote reference point.

6. The arrangement according to claim 1 wherein said third means is a collimated light beam source and said level indicating means is fixedly arranged relative to said third means so as to be operatively parallel to the light beam of said source.

* * * * *